（12） United States Patent
Jensen

(10) Patent No.: US 10,359,515 B2
(45) Date of Patent: Jul. 23, 2019

(54) ANGLE INDEPENDENT VELOCITY SPECTRUM DETERMINATION

(71) Applicant: B-K Medical Aps, Herlev (DK)

(72) Inventor: Jorgen Arendt Jensen, Horsholm (DK)

(73) Assignee: B-K Medical Aps, Herlev (DK)

( * ) Notice: Subject to any disclaimer, the term of this patent is extended or adjusted under 35 U.S.C. 154(b) by 200 days.

(21) Appl. No.: 15/632,825

(22) Filed: Jun. 26, 2017

(65) Prior Publication Data

US 2017/0293029 A1 Oct. 12, 2017

Related U.S. Application Data

(63) Continuation of application No. 14/646,770, filed as application No. PCT/IB2012/002527 on Nov. 28, 2012, now Pat. No. 9,702,972.

(51) Int. Cl.
| | | |
|---|---|---|
| *G01S 15/89* | (2006.01) |
| *A61B 8/06* | (2006.01) |
| *A61B 8/08* | (2006.01) |
| *A61B 8/14* | (2006.01) |
| *G01S 15/58* | (2006.01) |
| *G01S 7/52* | (2006.01) |
| *G01P 5/22* | (2006.01) |
| *G01P 5/24* | (2006.01) |

(52) U.S. Cl.
CPC .............. *G01S 15/588* (2013.01); *A61B 8/06* (2013.01); *A61B 8/14* (2013.01); *A61B 8/5207* (2013.01); *G01P 5/22* (2013.01); *G01P 5/244* (2013.01); *G01S 7/5202* (2013.01); *G01S 15/8915* (2013.01); *G01S 15/8984* (2013.01); *G01S 15/8927* (2013.01)

(58) Field of Classification Search
CPC .. G01S 15/588; G01S 7/5202; G01S 15/8915; G01S 15/8984; G01S 15/8927; A61B 8/14; A61B 8/5207; A61B 8/06; G01P 5/244; G01P 5/22
See application file for complete search history.

(56) References Cited

U.S. PATENT DOCUMENTS

| | | | | |
|---|---|---|---|---|
| 6,148,224 A * | 11/2000 | Jensen | ...................... | G01P 3/64 |
| | | | | 324/306 |
| 6,535,835 B1 * | 3/2003 | Rubin | ...................... | A61B 8/06 |
| | | | | 702/159 |
| 7,736,314 B2 * | 6/2010 | Beach | ................ | A61B 5/02007 |
| | | | | 181/101 |
| 9,066,679 B2 * | 6/2015 | Beach | ................ | A61B 5/02007 |

(Continued)

FOREIGN PATENT DOCUMENTS

| | | | | |
|---|---|---|---|---|
| EP | 2926147 A1 * | 10/2015 | ......... | G01S 15/8984 |
| WO | WO-2014083373 A1 * | 6/2014 | ......... | G01S 15/8984 |

*Primary Examiner* — Daniel Pihulic
(74) *Attorney, Agent, or Firm* — Anthony M. Del Zoppo, III; Daughterty & Del Zoppo Co., LPA

(57) ABSTRACT

An ultrasound imaging system (100) includes a transducer array (102) that emits an ultrasound beam and produces at least one transverse pulse-echo field that oscillates in a direction transverse to the emitted ultrasound beam and that receive echoes produced in response thereto and a spectral velocity estimator (110) that determines a velocity spectrum for flowing structure, which flows at an angle of 90 degrees and flows at angles less than 90 degrees with respect to the emitted ultrasound beam, based on the received echoes.

20 Claims, 3 Drawing Sheets

(56) References Cited

U.S. PATENT DOCUMENTS

| | | | | |
|---|---|---|---|---|
| 9,192,359 B2 * | 11/2015 | Flynn | ............... | G01S 15/8984 |
| 9,702,972 B2 * | 7/2017 | Jensen | ............... | G01S 15/8984 |
| 2006/0079782 A1 * | 4/2006 | Beach | ............... | A61B 5/02007 |
| | | | | 600/450 |
| 2010/0286522 A1 * | 11/2010 | Beach | ............... | A61B 5/02007 |
| | | | | 600/441 |
| 2014/0371594 A1 * | 12/2014 | Flynn | ............... | G01S 15/8984 |
| | | | | 600/454 |
| 2015/0331103 A1 * | 11/2015 | Jensen | ............... | G01S 15/8984 |
| | | | | 367/7 |
| 2017/0293029 A1 * | 10/2017 | Jensen | ............... | G01S 15/8984 |

* cited by examiner

ANGLE INDEPENDENT VELOCITY SPECTRUM DETERMINATION

TECHNICAL FIELD

The following relates to angle independent velocity spectrum determination and is described with particular application to ultrasound imaging.

BACKGROUND

An ultrasound scanner has been used to estimate a velocity spectrum for flowing structure in an object or subject of interest at a given depth and visually present the velocity distribution as a function of time in a spectrogram. The spectrogram has been calculated by measuring a sampled signal at the given depth and then employing a Fourier transform on the received data. This is discussed in Baker, "Pulsed ultrasonic Doppler blood-flow sensing," IEEE Trans. Son. Ultrason., SU-17:170-185 (1970), Evans et al., "Doppler Ultrasound, Physics, Instrumentation, and Clinical Applications: John Wiley & Sons, New York (1989), and Jensen, "Estimation of Blood Velocities Using Ultrasound: A Signal Processing Approach," Cambridge University Press, New York (1996).

For the display, the spectra are stacked side-by-side to show the time evolution of the velocity distribution. The relation between the velocity of the flowing structure and the measured frequency ($f_p$) can be represented as shown in EQUATION 1:

$$f_p = \frac{2v_z}{c} f_0 = \frac{2|\vec{v}|\cos\Theta}{c} f_0, \qquad \text{EQUATION 1}$$

where $f_0$ is the frequency of the emitted ultrasound beam, c is the speed of sound, $v_z$ is the structure velocity in the axial direction, and $\Theta$ is the angle between the structure velocity vector and the ultrasound beam. With this approach, only the axial velocity component is measured, and this measurement should be corrected for the angle $\Theta$. However, when $\Theta=90$ degrees, $\cos\Theta=0$, no velocity can be found. As such, this approach cannot be used for measuring velocity in vessels that are transverse to the ultrasound beam direction.

SUMMARY

Aspects of the application address the above matters, and others.

In one aspect, an ultrasound imaging system includes a transducer array that emits an ultrasound beam and produces at least one transverse pulse-echo field that oscillates in a direction transverse to the emitted ultrasound beam and that receive echoes produced in response thereto and a velocity processor that determines a velocity spectrum for flowing structure, which flows at an angle of 90 degrees and flows at angles less than 90 degrees with respect to the emitted ultrasound beam, based on the received echoes.

In another aspect, a method includes receiving echoes in response to emitting an ultrasound beam and at least one transverse pulse-echo field that oscillates in a direction transverse to the emitted ultrasound beam and determining a velocity spectrum for flowing structure, which flows at an angle of 90 degrees and flows at angles less than 90 degrees with respect to the emitted ultrasound beam, based on the received echoes.

In another aspect, a velocity processor includes a first spectral velocity estimator that estimates spectral velocity components in response to an angle between a velocity vector and the ultrasound beam being less than a first threshold angle, which does not include ninety degrees, wherein the first spectral velocity estimator estimates the spectral velocity components based on a measured frequency and a second spectral velocity estimator that estimates spectral velocity components in response to the angle between the velocity vector and the ultrasound beam being greater than the first threshold angle, which include ninety degrees, wherein the second spectral velocity estimator estimates the spectral velocity components based on a correlation of the received echoes.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

Figure 1:
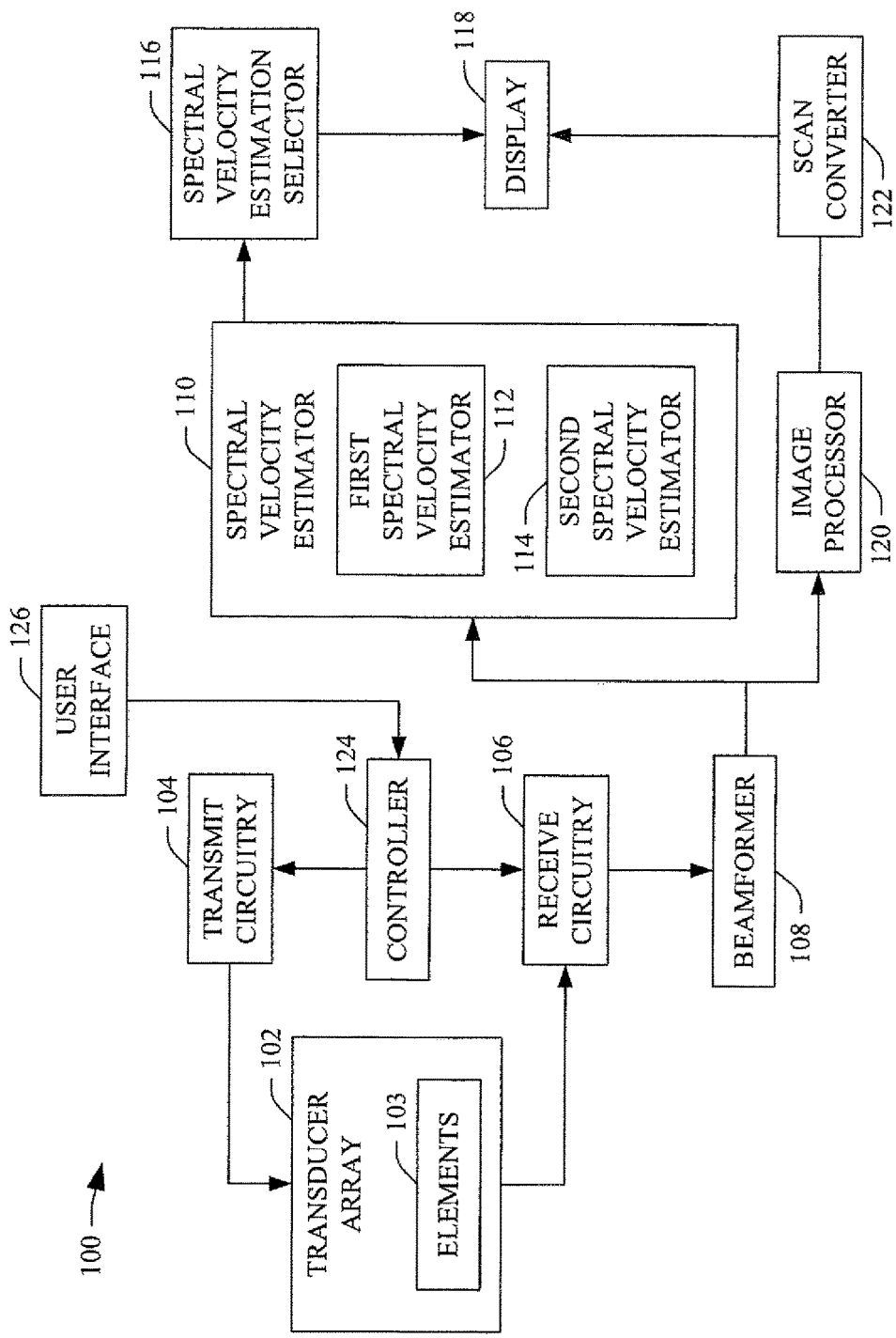
FIG. 1 illustrates an example ultrasound imaging scanner that includes a spectral velocity estimator with a first spectral velocity estimator and a second spectral velocity estimator, which estimates spectral velocities, even where the angle between the velocity vector of the structure and the ultrasound beam is ninety degrees.

FIG. 1 schematically illustrates an example ultrasound imaging system 100.

The ultrasound imaging system 100 includes a transducer array 102 with an array of transducer elements 103, which are configured to transmit ultrasound signals and receive echo signals. In one non-limiting instance, the array of transducer elements 103 is a 1D array with 64, 192, etc. elements. In another instance, the array of transducer elements 103 is a 2D array with 32×32, 64×64, etc. elements. It is to be appreciated that the 1D and/or 2D arrays of transducer elements 103 can include more or less elements. Furthermore, the transducer array 102 can be linear, curved, and/or otherwise shaped, and/or fully populated and/or sparse.

Transmit circuitry 104 generates pulses that excite a predetermined set of the transducer elements 103 to emit one or more ultrasound beams into a scan field of view, and receive circuitry 106 receives echoes generated in response to the transmitted ultrasound beams interacting with (generally stationary and/or flowing) structure in the scan field of view. In one instance, the transmit circuitry 104 is operated so that an axial pulse-echo field oscillates in the axial direction along the axis of the emitted ultrasound beam and at least one lateral or transverse (i.e., azimuth and/or elevation) pulse-echo field oscillates in a transverse direction, which is generally perpendicular to the emitted ultrasound beam, and different sets of elements 103 (e.g., sets of thirty-two (32) elements, etc.) receive echoes corresponding to the different pulse-echo fields.

Operation of the transmit circuitry 104 and the receive circuitry 106, as discussed in the preceding paragraph, with respect to emitting multiple different oscillation fields that are transverse to each other, can be achieved using the transverse oscillation (TO) approach. The TO approach with respect to the axial and one transverse directions is discussed in J. A. Jensen and P. Munk, "A New Method for Estimation of Velocity Vectors," IEEE Trans. Ultrason., Ferroelec., Freq. Contr., vol. 45, pp. 837-851 (1998), J. Udesen and J. A. Jensen, "Investigation of Transverse Oscillation Method," IEEE Trans. Ultrason., Ferroelec., Freq. Contr., vol. 53, pp. 959-971 (2006), EP19970928135, titled "Apparatus and Method for Determining Movement and Velocities of Moving Objects," and WO/2000/068678A1, title "Estimation of vector velocity." The TO approach with respect to the axial and multiple transverse directions is discussed in International patent application serial number PCT/IB2011/002383, titled Three Dimensional (3D) Transverse Oscillation Vector Velocity Ultrasound Imaging, and filed Oct. 12, 2011, the entirety of which is incorporated herein by reference.

A beamformer 108 processes the echoes, for example, by applying time delays, weighting the channels, summing, and/or otherwise processing the received echoes. This includes processing the echoes and producing data for determining a velocity spectrum for flowing structure in the axial and at least one of the azimuth or elevation directions. The illustrated beamformer 312 also produces data for generating data for constructing images in A-mode, B-mode, and/or other modes.

A spectral velocity estimator 110 processes the beamformed data and estimates a velocity spectrum. A first spectral velocity estimator 112 estimates a velocity spectrum based on EQUATION 1. The output of the first spectral velocity estimator 112 is employed when the angle between the velocity vector of the flowing structure and the ultrasound beam (i.e., $\Theta$) is less than ninety (90) degrees, for example, in a range from zero (0) to seventy (70) degrees. Angle correction can be employed for $\Theta>0$. At $\Theta=90$ degrees, as discussed herein, EQUATION 1 cannot be used to estimate a velocity.

A second spectral velocity estimator 114 estimates a velocity spectrum based on the TO approach in which a pulse-echo oscillation transverse to the ultrasound beam is made during emission or in receive processing, and a velocity spectrum estimation is made based on a correlation of the received signal. The second spectral velocity estimator 114 estimates the velocity spectrum as a function of time, like the first spectral velocity estimator 112, but can additionally estimate a velocity even at $\Theta=90$ degrees.

As described in greater below, the second spectral velocity estimator 114 estimates a velocity spectrum, in one instance, based on auto and cross-correlation functions of the received signals (referred to herein as a second order approach), and, in another instance, based on auto-correlation functions of the received signals, either without an axial or without a lateral velocity component (referred to herein as a fourth order approach).

Both the second order and the fourth order approaches can reliably determine the velocity at 90 degrees, unlike an estimation based on EQUATION 1 which, at 90 degrees, yields zero velocity. Thus, an operator can orient the transducer array 102 in any direction and still measure velocity. Furthermore, the velocity range tends to be higher for the fourth order approach relative to the estimation based on EQUATION 1 as the lateral wavelength is larger than the axial wavelength. This may be beneficial for either keeping the pulse repetition frequency low or for maintaining a high maximum detectable velocity.

The spectral velocity estimator 110 can be implemented via a processor(s) (e.g., microprocessor, central processing unit or cpu, etc.) of a computing system(s) executing a computer readable instruction(s) encoded or embedded on a computer readable storage medium such as physical memory or other non-transitory medium. Additionally or alternatively, at least one instruction can be carried by a carrier wave, a signal, or other transitory or non-computer readable storage medium.

A spectral velocity estimation selector 116 selects one of the velocity spectrums, either the velocity spectrum from the first spectral velocity estimator 112 or the velocity spectrum from the second spectral velocity estimator 114, for visual presentation. In one instance, the selection between the two spectra is based on an estimated angle at the range gate, which can be obtained using a TO estimator without additional beamforming. The selected velocity spectrum can be presented via a display 118, for example, as velocity distribution as a function of time. In a variation, the spectral velocity estimation selector 116 selects a suitable estimation approach prior to any estimation, and only one of the estimators 112 or 114, the estimator corresponding to the selected approach, estimates the velocity spectrum.

In one non-limiting instance, the spectral velocity estimation selector 116 selects the velocity spectrum from the first spectral velocity estimator 112 or the spectral velocity estimation from the second spectral velocity estimator 114 based on a predetermined angle threshold. For example, in one instance, the predetermined angle threshold is 60 degrees, and the spectral velocity estimation selector 116 selects the spectral velocity estimation from the first spectral velocity estimator 112 when the estimated angle is less than the threshold and selects the spectral velocity estimation from the second spectral velocity estimator 114 otherwise. Other suitable angles such as 50, 70 or an angle there between are also contemplated herein. The threshold can be default, protocol specific, user defined, etc.

In a variation, the first spectral velocity estimator 112 is omitted, and the second spectral velocity estimator 114 estimates the velocity spectrum for all angles.

An image processor 120 processes the beamformed data, generating image data. For example, for B-mode, the image processor 120 processes the data and generates a sequence of focused, coherent echo samples along focused scanlines of a scanplane. Other modes are also contemplated herein. The image processor 120 may also be configured to process the scanlines to lower speckle and/or improve specular reflector delineation via spatial compounding and/or perform other processing such as FIR filtering, IIR filtering, etc.

A scan converter 122 scan converts the image data, generating data for display, e.g., by converting the data to the coordinate system of the display 118. The image data can additionally or alternatively be presented via the display 118. Such presentation can be in an interactive graphical user interface (GUI), which allows the user to selectively rotate, scale, and/or manipulate the displayed data. Such interaction can be through a mouse, a keyboard, touchscreen controls, etc.

A controller 124 controls one or more of the transmit circuitry 104 or receive circuitry 106. Such control can be based on available modes of operation (e.g., spectrogram, B-mode, etc.) of the system 100. A particular mode can be activated by one or more signals indicative of input from a user via a user interface (UI) 126. The UI 126 may include one or more input devices (e.g., a button, a knob, a slider, a touch pad, etc.) and/or one or more output devices (e.g., a display screen, lights, a speaker, etc.).

Figure 2:
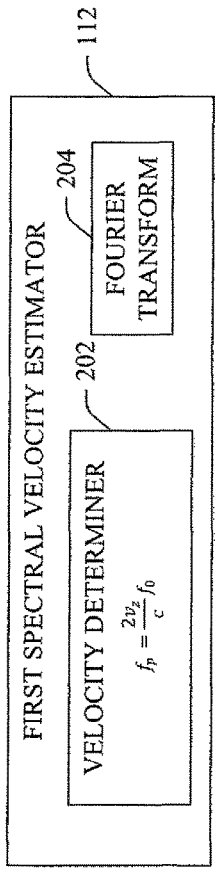
FIG. 2 illustrates an example of the first spectral velocity estimator which determines a spectral velocity based on emitted ultrasound beam frequency and a measured frequency.
Figure 3:
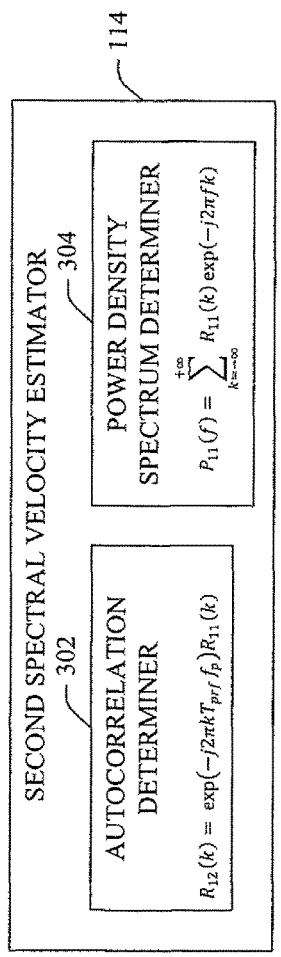
FIG. 3 illustrates an example of the second spectral velocity estimator which determines a spectral velocity based on a second order approach.
Figure 4:
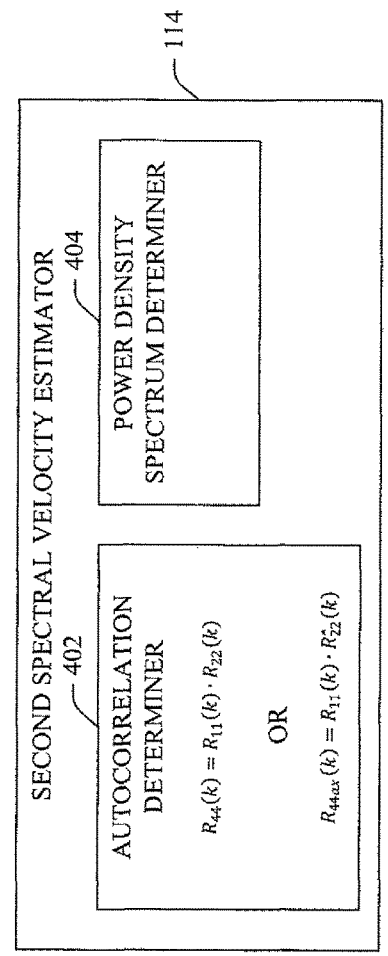
FIG. 4 illustrates an example of the second spectral velocity estimator which determines a spectral velocity based on a fourth order approach.

FIGS. 2, 3 and 4 illustrate examples of the spectral velocity estimator 110. FIG. 2 shows an example of the first spectral velocity estimator 112, and FIGS. 3 and 4 shows examples of the second spectral velocity estimator 114.

In FIG. 2, the first spectral velocity estimator 112 includes a velocity determiner 202, which utilizes EQUATION 1 to determine the axial velocity of flowing structure of interest. The first spectral velocity estimator 112 further includes Fourier transform 204, which is applied to the axial velocity to determine the spectral velocity. The axial velocity is determined over time and visually displayed as a function of time when the output of the first spectral velocity estimator 112 is selected by the spectral velocity estimation selector 116 (FIG. 1).

For FIGS. 3 and 4, the TO approach can yield two beams focused in parallel, namely, an in-phase (I) component and a quadrature (Q) component. This complex signal can, at one fixed depth, be described as shown in EQUATION 2:

$$r_{sq}(i) = \cos(2\pi f_p i T_{prf}) \exp(j2\pi f_x i T_{prf}),  \quad \text{EQUATION 2}$$

where i is the emission number, $T_{prf}$ is the pulse repetition time and $f_p$ is the received axial frequency, which can be defined as shown in EQUATION 3:

$$f_p = \frac{2v_z}{c} f_0. \quad \text{EQUATION 3}$$

where $f_0$ is the emitted frequency, c is the speed of sound, and $v_z$ is the axial velocity component.

The temporal Hilbert transform of EQUATION 1 is shown in EQUATION 4:

$$r_{sqh}(i) = \sin(2\pi f_p i T_{prf}) \exp(j2\pi f_x i T_{prf}). \quad \text{EQUATION 4}$$

Combining EQUATIONS 1 and 3 and using Euler's equations produces EQUATIONS 5 and 6

$$r_{sq} = \tfrac{1}{2}(\exp(j2\pi i T_{prf}(f_x+f_p)) + \exp(j2\pi i T_{prf}(f_x-f_p))), \text{ and} \quad \text{EQUATION 5:}$$

$$r_{sqh}(i) = \frac{1}{2j}(\exp(j2\pi i T_{prf}(f_x+f_p)) - \exp(j2\pi i T_{prf}(f_x-f_p))). \quad \text{EQUATION 6}$$

Adding and subtracting EQUATIONS 5 and 6 produces two additional equations, EQUATIONS 7 and 8:

$$r_1(i) = r_{sq}(i) + j r_{sqh}(i) = \exp(j2\pi i T_{prf}(f_x+f_p)), \text{ and} \quad \text{EQUATION 7}$$

$$r_2(i) = r_{sq}(i) - j r_{sqh}(i) = \exp(j2mi T_{prf}(f_x-f_p)). \quad \text{EQUATION 8}$$

In FIG. 3, the second spectral velocity estimator 114 includes an autocorrelation determiner 302, which determines an autocorrelation of the received signal based on EQUATION 9:

$$\begin{aligned} R_{12}(k) &= \sum_{k=-\infty}^{+\infty} r_1(i) r_2(i+k), \\ &= \sum_{k=-\infty}^{+\infty} \exp(j2\pi i T_{prf}(f_x+f_p)) \exp(j2\pi(i+k) T_{prf}(f_x-f_p)) \\ &= \exp(j2\pi k T_{prf}(f_x-f_p)) \sum_{k=-\infty}^{+\infty} \exp(j2\pi k T_{prf}(f_x+f_p+f_x-f_p)) \\ &= \exp(j2\pi k T_{prf}(f_x-f_p)) \sum_{k=-\infty}^{+\infty} \exp(j2\pi k T_{prf} 2f_x) \\ &= \exp(-j2\pi k T_{prf} f_p) \sum_{k=-\infty}^{+\infty} \exp(j2\pi i T_{prf} f_x) \exp(j2\pi(i+k) T_{prf} f_x) \\ &= \exp(-j2\pi k T_{prf} f_p) R_{11}(k). \end{aligned} \quad \text{EQUATION 9}$$

When the frequency $$f_P = \frac{2v_z}{c} f_0$$

is zero, there is no axial velocity component ($v_z=0$), and the cross-correlation $R_{12}(k)$ between the spatial in-phase and quadrature signal directly equals the autocorrelation $R_{11}(k)$.

The modulation of the cross-correlation function by the factor $\exp(j2mkT_{prf}f_p)$ can be compensated for by estimating the axial velocity and thereby $f_p$, and then multiply $R_{12}(k)$ by the compensation factor $R_c(k) = \exp(j2\pi k T_{prf} f_p)$. The axial velocity can be found from a normally focused line lying between the two spatial beams and then employing an autocorrelation estimator, rending EQUATION 10:

$$\hat{v}_z = \frac{c f_{prf}}{2\pi f_0} \arctan\left( \frac{\sum_{i=1}^{N_c-1} y(i)x(i-1) - x(i)y(i-1)}{\sum_{i=1}^{N_c-1} x(i)x(i-1) + y(i)y(i-1)} \right), \quad \text{EQUATION 10}$$

where the received signal is $r(i) = x(i) + jy(i)$ and $r(i) = x(i) + jy(i)$. Alternatively, the velocity can be found using, for example, the approach discussed in O. Bonnefous, P. Pesque and X. Bernard: "A new velocity estimator for color flow mapping", Proc. IEEE Ultrasonics Symposium, pp. 855-

860, 1986, T. Loupas, J. T. Powers, R. W. Gill: An axial velocity estimator for ultrasound blood flow imaging, based on a full evaluation of the Doppler equation by means of a two-dimensional autocorrelation approach, IEEE Trans. on Ultrasonics, Ferroelec. and Freq. control, vol. 43, pp. 672-688, 1995, Jensen, J A 2001, 'A new estimator for vector velocity estimation', IEEE Transactions on Ultrasonics, Ferroelectrics and Frequency Control, vol 48, no. 4, pp. 886-894 or Jensen, J A 1996, Estimation of Blood Velocities Using Ultrasound: A Signal Processing Approach. Cambridge University Press, New York.

In FIG. 3, the second spectral velocity estimator 114 further includes a power density spectrum determiner 304, which determines a velocity spectrum based on EQUATION 11:

$$P_{11}(f) = \sum_{k=-\infty}^{+\infty} R_{11}(k)\exp(-j2\pi fk). \quad \text{EQUATION 11}$$

The approach described in connection with FIG. 3 is referred to herein as the second order approach.

In FIG. 4, the second spectral velocity estimator 114 includes an autocorrelation determiner 402, which determines an autocorrelation of the received signal based on EQUATION 12 or 13 (EQUATION 13 being the complex conjugate of EQUATION 12):

$$R_{44}(k) = R_{11}(k) \cdot R_{22}(k), \quad \text{EQUATION 12}$$

or $$R_{44ax}(k) = R_{11}(k) \cdot R_{22}^*(k), \quad \text{EQUATION 13}$$

where $R_{11}(k)$ and $R_{22}(k)$ are respective autocorrelations $R_{11}(k) = \sum_{i=-\infty}^{+\infty} r_1(i)r_1(i+k)$ and $R_{22}(k) = \sum_{i=-\infty}^{+\infty} r_2(i)r_2(i+k)$. In EQUATION 12, the axial component is eliminated, and in EQUATION 13, the lateral component is eliminated.

In FIG. 4, the second spectral velocity estimator 114 further includes a power density spectrum determiner 404, which determines a velocity spectrum based on EQUATION 14:

$$P_{44}(f) = \sum_{k=-\infty}^{+\infty} R_{44}(k)\exp(-j2\pi fk), \quad \text{EQUATION 14}$$

The approach described in connection with FIG. 4 is referred to herein as the fourth order approach.

Figure 5:
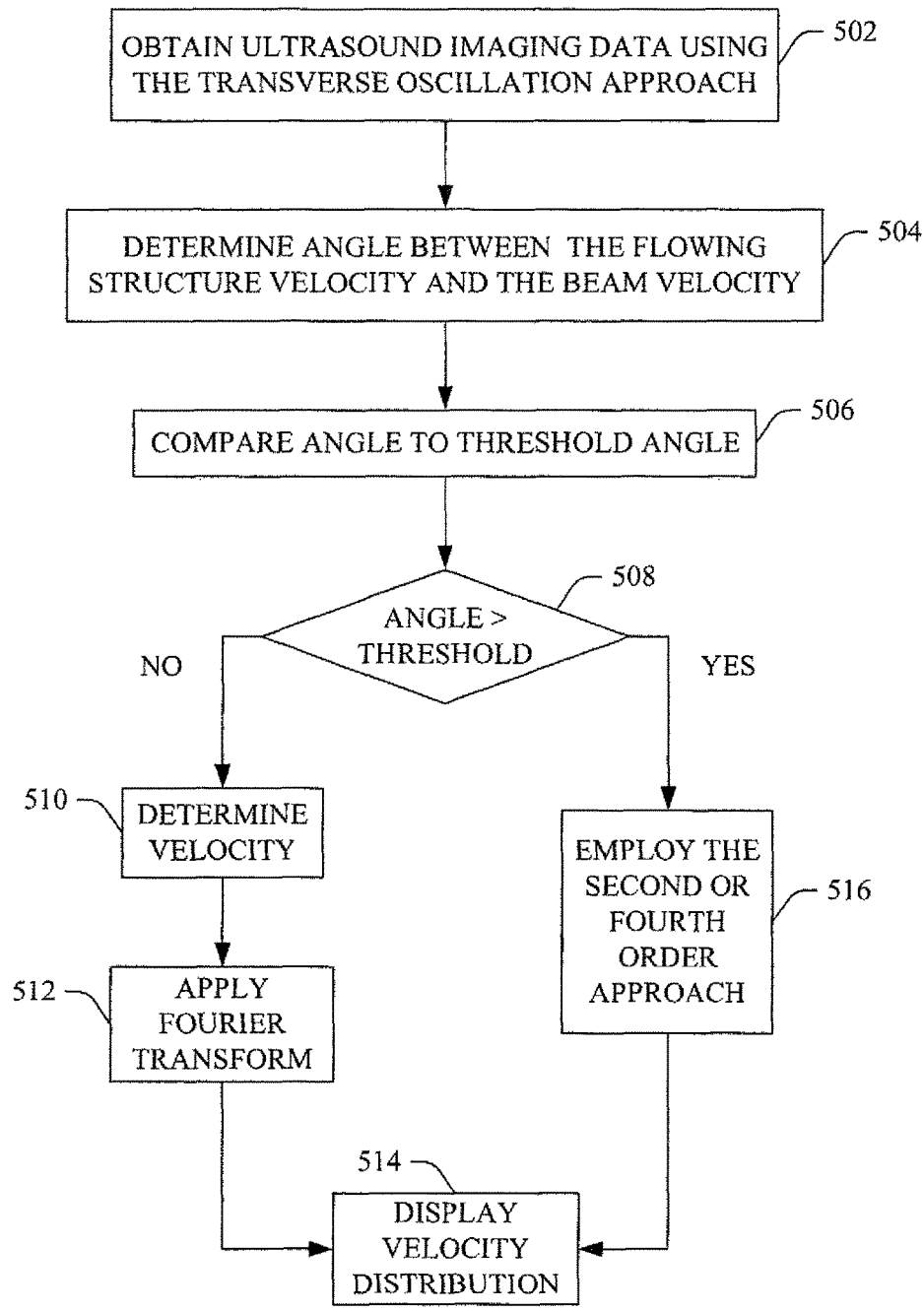
FIG. 5 illustrates a method in accordance with the spectral velocity estimator embodiments disclosed herein.

FIG. 5 illustrates an example method for employing the ultrasound imaging system discussed herein.

It is to be understood that the following acts are provided for explanatory purposes and are not limiting. As such, one or more of the acts may be omitted, one or more acts may be added, one or more acts may occur in a different order (including simultaneously with another act), etc.

At 502, ultrasound imaging data is obtained using the TO approach.

At 504, the angle Θ between the velocity vector of the flowing structure and the ultrasound beam is estimated.

At 506, the estimated angle is compared with a predetermined angle threshold. As discussed herein, in one instance, the threshold has value in a range between 50 and 70 degrees.

At 508, it is determined whether the estimated angle satisfies the threshold.

If not, then at 510 a velocity determiner determines a velocity of the flowing structure based on EQUATION 1, at 512, a Fourier transform is applied to the velocity, and at 514, the velocity distribution is displayed as a function of time.

If so, then at 516 either the second order power density spectrum (FIG. 3) or the fourth order power density spectrum (FIG. 4) is employed to determine velocity spectrum, and at 514 the velocity distribution is displayed as a function of time.

In a variation, acts 504-508 are performed after acts 510, 512 and 516, and one of the estimations is selected based on an outcome of act 508.

The methods described herein may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound imaging system, comprising:
   a transducer array that emits an ultrasound beam and produces at least one transverse pulse-echo field that oscillates in a direction transverse to the emitted ultrasound beam and that receive echoes produced in response thereto; and
   a velocity processor that determines a velocity spectrum for flowing structure, which flows at an angle of 90 degrees and or less with respect to the emitted ultrasound beam, based on the received echoes,
   wherein the velocity processor determines the velocity spectrum based on an autocorrelation in response to an angle between a velocity vector of the flowing structure and the ultrasound beam being greater than sixty degrees.

2. The system of claim 1, wherein the velocity processor determines the autocorrelation based on a cross-correlation of between spatial in-phase and quadrature signals.

3. The system of claim 2, wherein the autocorrelation equals the cross-correlation in response to an axial velocity component equal to zero.

4. The system of claim 2, wherein a modulation of the cross-correlation is compensated for by multiplying the cross-correlation by a compensation factor.

5. The system of claim 4, wherein the compensation factor is based on an axial velocity estimated from a normally focused line lying between two spatial beams and employing an autocorrelation estimator.

6. The system of claim 1, wherein the velocity processor determines the autocorrelation based on an autocorrelation of spatial in-phase signals and an autocorrelation of quadrature signals.

7. The system of claim 6, wherein the autocorrelation does not include an axial velocity component.

8. The system of claim 1, wherein the velocity processor determines the autocorrelation based on an autocorrelation of spatial in-phase signals and a complex conjugate of an autocorrelation of quadrature signals.

9. The system of claim 8, wherein the autocorrelation does not include a lateral velocity component.

10. The system of claim 1, wherein the velocity processor determines the velocity spectrum based on a measured frequency in response to the angle being less than sixty degrees.

11. The system of claim 1, further comprising:
a display that visually presents the velocity spectrum.

12. An ultrasound imaging system, comprising:
a transducer array that emits an ultrasound beam and produces at least one transverse pulse-echo field that oscillates in a direction transverse to the emitted ultrasound beam and that receive echoes produced in response thereto; and
a velocity processor that determines a velocity spectrum for flowing structure, which flows at an angle of 90 degrees and or less with respect to the emitted ultrasound beam, based on the received echoes,
wherein the velocity processor determines the velocity spectrum based on an autocorrelation, and wherein the velocity processor determines the autocorrelation based on a cross-correlation of between spatial in-phase and quadrature signals.

13. The system of claim 12, wherein the velocity processor determines the velocity spectrum based on the autocorrelation in response to an angle between a velocity vector of the flowing structure and the ultrasound beam being greater than sixty degrees.

14. The system of claim 12, wherein the velocity processor determines the velocity spectrum based on a measured frequency in response to the angle being less than sixty degrees.

15. An ultrasound imaging system, comprising:
a transducer array that emits an ultrasound beam and produces at least one transverse pulse-echo field that oscillates in a direction transverse to the emitted ultrasound beam and that receive echoes produced in response thereto; and
a velocity processor that determines a velocity spectrum for flowing structure, which flows at an angle of 90 degrees and or less with respect to the emitted ultrasound beam, based on the received echoes,
wherein the velocity processor determines the velocity spectrum based on an autocorrelation, and wherein the velocity processor determines the autocorrelation based on a cross-correlation of spatial in-phase signals and an autocorrelation of quadrature signals.

16. The system of claim 15, wherein the velocity processor determines the velocity spectrum based on the autocorrelation in response to an angle between a velocity vector of the flowing structure and the ultrasound beam being greater than sixty degrees.

17. The system of claim 15, wherein the velocity processor determines the velocity spectrum based on a measured frequency in response to the angle being less than sixty degrees.

18. An ultrasound imaging system, comprising:
a transducer array that emits an ultrasound beam and produces at least one transverse pulse-echo field that oscillates in a direction transverse to the emitted ultrasound beam and that receive echoes produced in response thereto; and
a velocity processor that determines a velocity spectrum for flowing structure, which flows at an angle of 90 degrees and or less with respect to the emitted ultrasound beam, based on the received echoes,
wherein the velocity processor determines the velocity spectrum based on an autocorrelation, and wherein the velocity processor determines the autocorrelation based on a cross-correlation of spatial in-phase signals and a complex conjugate of an autocorrelation of quadrature signals.

19. The system of claim 18, wherein the velocity processor determines the velocity spectrum based on the autocorrelation in response to an angle between a velocity vector of the flowing structure and the ultrasound beam being greater than sixty degrees.

20. The system of claim 18, wherein the velocity processor determines the velocity spectrum based on a measured frequency in response to the angle being less than sixty degrees.

* * * * *